US009786432B2

(12) United States Patent
Zilbershlag

(10) Patent No.: US 9,786,432 B2
(45) Date of Patent: *Oct. 10, 2017

(54) COPLANAR ENERGY TRANSFER

(71) Applicant: Leviticus Cardio Ltd., Givat Shmuel (IL)

(72) Inventor: Michael Zilbershlag, Givat Shmuel (IL)

(73) Assignee: Leviticus Cardio Ltd., Givat Shmuel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/097,867

(22) Filed: Apr. 13, 2016

(65) Prior Publication Data

US 2016/0233023 A1 Aug. 11, 2016

Related U.S. Application Data

(63) Continuation of application No. 13/588,524, filed on Aug. 17, 2012, now Pat. No. 9,343,224.

(Continued)

(51) Int. Cl.
*A61M 1/12* (2006.01)
*H01F 38/14* (2006.01)
(Continued)

(52) U.S. Cl.
CPC ............. *H01F 38/14* (2013.01); *A61M 1/127* (2013.01); *A61N 1/3787* (2013.01); *A61N 1/37229* (2013.01)

(58) Field of Classification Search
CPC . H02J 5/005; H02J 7/025; H02J 17/00; H01F 38/14; B60L 11/182; A61M 1/127; A61N 1/3787; A61N 1/37229

(Continued)

(56) References Cited

U.S. PATENT DOCUMENTS 4,143,661 A * 3/1979 LaForge ............... A61N 1/3787
607/61
4,665,896 A * 5/1987 LaForge .............. A61M 1/1086
600/17

(Continued)

FOREIGN PATENT DOCUMENTS

WO 2007003351 A1 1/2007
WO 2013/085996 A1 6/2013

OTHER PUBLICATIONS

Dermott, J. & Bond, J., "Safety Considerations for Lithium-Ion Flight Batteries," Power Sources Conference, Orlando, Jun. 2014, 4 pages.

(Continued)

*Primary Examiner* — Thienvu Tran
*Assistant Examiner* — Brian K Baxter
(74) *Attorney, Agent, or Firm* — Brown Rudnick LLP

(57) ABSTRACT

An external transmitter inductive coil can be provided in, on, or with a belt designed to be placed externally around a part of a body of a patient. An implantable device (such as a VAD or other medical device) that is implanted within the patient's body has associated with a receiver inductive coil that gets implanted within that part of the patient's body along with the device. The externally-located transmitter inductive coil inductively transfers electromagnetic power into that part of the body and thus to the receiver inductive coil. The implanted receiver inductive coil thus wirelessly receives the inductively-transferred electromagnetic power, and operates the implant.

20 Claims, 10 Drawing Sheets

Related U.S. Application Data

(60) Provisional application No. 61/540,140, filed on Sep. 28, 2011, provisional application No. 61/525,272, filed on Aug. 19, 2011.

(51) Int. Cl.
*A61N 1/378* (2006.01)
*A61N 1/372* (2006.01)

(58) Field of Classification Search
USPC .................................................. 307/104
See application file for complete search history.

(56) References Cited

U.S. PATENT DOCUMENTS

| | | | |
|---|---|---|---|
| 4,906,229 A | 3/1990 | Wampler | |
| 4,957,504 A | 9/1990 | Chardack | |
| 5,089,017 A * | 2/1992 | Young | A61M 1/106 623/3.11 |
| 5,095,903 A | 3/1992 | DeBellis | |
| 5,507,629 A | 4/1996 | Jarvik | |
| 5,749,855 A | 5/1998 | Reitan | |
| 5,991,665 A * | 11/1999 | Wang | H02J 5/005 320/108 |
| 6,070,103 A | 5/2000 | Ogden | |
| 6,129,704 A | 10/2000 | Forman et al. | |
| 6,135,729 A | 10/2000 | Aber | |
| 6,280,377 B1 | 8/2001 | Talpade | |
| 6,421,889 B1 | 7/2002 | Chien | |
| 6,527,699 B1 | 3/2003 | Goldowsky | |
| 6,531,847 B1 | 3/2003 | Tsukamoto et al. | |
| 6,761,681 B2 | 7/2004 | Schmid et al. | |
| 6,772,011 B2 | 8/2004 | Dolgin | |
| 6,891,353 B2 | 5/2005 | Tsukamoto et al. | |
| 7,433,794 B1 | 10/2008 | Berdichevsky et al. | |
| 7,613,497 B2 | 11/2009 | Govari et al. | |
| 7,650,192 B2 | 1/2010 | Wahlstrand | |
| 7,738,965 B2 | 6/2010 | Phillips et al. | |
| 7,741,734 B2 | 6/2010 | Joannopoulos et al. | |
| 7,821,230 B2 | 10/2010 | Studyvin et al. | |
| 7,825,543 B2 | 11/2010 | Karalis et al. | |
| 7,825,629 B2 | 11/2010 | Studyvin et al. | |
| 7,825,776 B2 | 11/2010 | Smith et al. | |
| 7,928,691 B2 | 4/2011 | Studyvin et al. | |
| 7,956,725 B2 | 6/2011 | Smith | |
| 8,075,472 B2 | 12/2011 | Zilbershlag et al. | |
| 8,129,865 B2 | 3/2012 | Krumme et al. | |
| 8,244,367 B2 | 8/2012 | Wahlstrand et al. | |
| 8,278,784 B2 | 10/2012 | Cook et al. | |
| 8,285,388 B2 | 10/2012 | Wahlstrand | |
| 8,579,789 B1 | 11/2013 | Zilbershlag | |
| 8,585,572 B2 | 11/2013 | Mehmanesh | |
| 8,840,539 B2 | 9/2014 | Zilbershlag | |
| 8,845,510 B2 | 9/2014 | Zilbershlag | |
| 8,961,389 B2 | 2/2015 | Zilbershlag | |
| 8,979,728 B2 | 3/2015 | Zilbershlag | |
| 9,343,224 B2 * | 5/2016 | Zilbershlag | H01F 38/14 |
| 2003/0163020 A1 | 8/2003 | Frazier | |
| 2004/0014315 A1 | 1/2004 | Lai et al. | |
| 2004/0054251 A1 | 3/2004 | Liotta | |
| 2004/0115038 A1 | 6/2004 | Nuesser et al. | |
| 2005/0220636 A1 | 10/2005 | Henein et al. | |
| 2006/0085039 A1 * | 4/2006 | Hastings | A61N 1/0587 607/9 |
| 2006/0085041 A1 * | 4/2006 | Hastings | A61N 1/0587 607/33 |
| 2007/0132587 A1 | 6/2007 | Smith et al. | |
| 2007/0182578 A1 | 8/2007 | Smith | |
| 2007/0255223 A1 * | 11/2007 | Phillips | A61N 1/08 604/179 |
| 2008/0041930 A1 | 2/2008 | Smith et al. | |
| 2008/0109054 A1 * | 5/2008 | Hastings | A61N 1/0587 607/127 |
| 2008/0238680 A1 | 10/2008 | Posamentier et al. | |
| 2008/0292478 A1 | 11/2008 | Baykut et al. | |
| 2009/0243813 A1 | 10/2009 | Smith et al. | |
| 2010/0045114 A1 | 2/2010 | Sample et al. | |
| 2010/0052811 A1 | 3/2010 | Smith et al. | |
| 2010/0076247 A1 | 3/2010 | Zilbershlag et al. | |
| 2010/0081379 A1 | 4/2010 | Cooper et al. | |
| 2010/0187913 A1 | 7/2010 | Smith et al. | |
| 2010/0197994 A1 * | 8/2010 | Mehmanesh | A61M 1/1072 600/18 |
| 2011/0080051 A1 | 4/2011 | Lee et al. | |
| 2011/0193688 A1 * | 8/2011 | Forsell | A61N 1/37229 340/10.4 |
| 2011/0278948 A1 * | 11/2011 | Forsell | H02J 7/025 307/104 |
| 2011/0301668 A1 * | 12/2011 | Forsell | A61N 1/37223 607/60 |
| 2012/0123284 A1 * | 5/2012 | Kheradvar | A61B 5/0031 600/509 |
| 2012/0146575 A1 | 6/2012 | Armstrong et al. | |
| 2012/0150291 A1 * | 6/2012 | Aber | H02J 7/025 623/3.14 |
| 2012/0235502 A1 * | 9/2012 | Kesler | H03H 7/40 307/104 |
| 2012/0239118 A1 | 9/2012 | Ozawa et al. | |
| 2013/0043736 A1 | 2/2013 | Zilbershlag | |
| 2013/0053624 A1 | 2/2013 | Zilbershlag | |
| 2013/0141109 A1 | 6/2013 | Love et al. | |
| 2014/0031607 A1 | 1/2014 | Zilbershlag et al. | |
| 2014/0163307 A1 | 6/2014 | Zilbershlag | |
| 2014/0236172 A1 * | 8/2014 | Hastings | A61N 1/0565 606/129 |
| 2016/0023004 A1 * | 1/2016 | Forsell | A61N 1/3787 607/61 |

OTHER PUBLICATIONS

Farmer, J. et al., "Wireless Battery Management System for Safe High-Capacity Energy Storage," 31st Annual Battery Seminar (Orlando, FL), 2014, 4 pages.
Garcia, H.E. et al., "On-line State-of-Health and Remaining-Useful-Life Assessment of Batteries using Rapid Impedance Spectrum Measurements," 45th Power Sources Symposium, Las Vegas, Abstract 7.3, 2012, 4 pages.
International Search Report dated Jan. 30, 2009 for International Application No. PCT/IL2008/000604 (4Pages).
Patridge, C.J. & Love, C.T., "Impedance Spectroscopy Diagnostic for Monitoring Li-ion Batteries," 45th Power Sources Symposium, Las Vegas, Abstract 7.4, 2012, 4 pages.
Non Final Office Action dated Jan. 15, 2016 for U.S. Appl. No. 14/041,698 (8 Pages).
Response to Non Final Office Action dated May 26, 2016 for U.S. Appl. No. 14/041,698 (8 Pages).
Final Office Action dated Jun. 15, 2016 for U.S. Appl. No. 14/041,698 (7 Pages).
Response to Final Office Action dated Sep. 7, 2016 for U.S. Appl. No. 14/041,698 (7 Pages).
Notice of Allowance and Fees Due dated Jan. 6, 2017 for U.S. Appl. No. 14/041,698 (16 Pages).
Response to Final Office Action and Request for Examination filed Dec. 1, 2016 for U.S. Appl. No. 14/041,698 (12 Pages).
Advisory Action dated Oct. 5, 2016 for U.S. Appl. No. 14/041,698 (3 Pages).

* cited by examiner

COPLANAR ENERGY TRANSFER

STATEMENT OF RELATED APPLICATIONS

This application is a continuation of U.S. patent application Ser. No. 13/588,524, filed Aug. 17, 2012, which claims priority to U.S. Provisional Patent Application Ser. No. 61/525,272, filed Aug. 19, 2011, and U.S. Provisional Patent Application Ser. No. 61/540,140, filed Sep. 28, 2011, each of which is incorporated herein by reference in its entirety.

TECHNICAL FIELD

The invention relates to wireless energy transfer into the body of a patient to power wirelessly a device implanted within the patient's body.

BACKGROUND INFORMATION

Wireless power transfer for implanted medical devices is a known and well-studied subject. The traditional approach is TET (transcutaneous energy transfer), in which the energy source is directed toward the energy harvesting device with the goal to minimize RF exposure of the patient. In one commercial embodiment, the receiver coils are located under the patient's skin and the transmitter above the skin. Such TET systems are very sensitive to misalignment and movement of the implanted coil. Additionally, the coil implanted in a separate surgical procedure. Another shortcoming of the current TET solution is that the electromagnetic field density is so high that it can cause heating of the skin and even burns. That is, when the receiver is receiving energy, regular resistance losses within the coil can cause heating to the same volume of tissue receiving the electromagnetic radiation and add heating to it. When the transmitter attached to the receiver is transmitting energy, regular resistance losses within the transmitter coil can cause heating that adds to the receiver regular resistance losses heating and to the receiving electromagnetic radiation heating. The accumulated heat can become a complex issue. TET systems have also suffered setbacks due to complexity and lack of efficiency.

Because of the heating issues, there is no TET system commercially available for use with a ventricular assist device (VAD). In current VAD systems, the power needed for the pump is delivered via an external power pack by a transcutaneous power line. The exit site of the drive line from the abdomen provides a portal of entry for pathogens, making VAD recipients highly vulnerable to device-related infections. However infectious complications are not limited to VAD systems, as infections are common in many medical devices that use transcutaneous power line.

There have been many attempts to develop a superior wireless power transfer system for use with implanted medical devices. Some known wireless power transfer approaches are described in U.S. Pat. Nos. 6,772,011, 7,741, 734, 7,825,543, 7,613,497, 7,825,776, and 7,956,725 and in U.S. Patent Application Publication Nos. 2007-0132587, 2007-0182578, 2008-0041930, 2008-0238680, 2009-0243813, 2010-0045114, 2010-0052811, 2010-0081379, and 2010-0187913, all of which are incorporated herein by reference in their entireties.

SUMMARY OF THE INVENTION

In general, the invention relates to an external transmitter inductive coil that can be provided in, on, or with a belt designed to be placed externally around a part of a body of a patient. This embodiment suggests new approach for medical implant wireless power transfer, which will increase the safety and efficiency, and in parallel reduce the cumbersomeness of traditional TET use by simplify the surgery and placement process.

The transmitter inductive coil can be one, two, or more turns of an electrically-conductive material such as a metal wire. The patient can be a human or an animal, and the part of the body can be the arm, leg, head, or torso of the patient. An implantable device (such as a VAD or other medical device) that is implanted within that part of the patient's body has associated with it (for example, electrically coupled to it) a receiver inductive coil that gets implanted within that part of the patient's body along with the device. The externally-located transmitter inductive coil surrounds at least a portion of the implanted receiver inductive coil and inductively transfers electromagnetic power into that part of the body and thus to the receiver inductive coil. The implanted receiver inductive coil thus wirelessly receives the inductively-transferred electromagnetic power from the external transmitter coil, and the implanted receiver inductive coil provides that received power to the implanted implantable device to allow that device to operate. If the device is a VAD, then the power can be used to operate the pumping action of the VAD.

In one particular aspect, the invention involves a system for wirelessly powering an implantable device such as a medical device, and the system comprises a transmitter inductive coil and a receiver inductive coil. The transmitter inductive coil is configured to be disposed externally around a part of a body of a patient (whether human or animal) within which the implantable device is implanted and to inductively transfer electromagnetic power into that part of the body. The receiver inductive coil is associated with the implantable device and is configured to be implanted within that part of the patient's body along with the implantable device to wirelessly receive the inductively-transferred electromagnetic power and provide that received power to the implanted implantable device.

Embodiments according to this aspect of the invention can have various features. For example, the externally-located transmitter inductive coil can be one, two, or more turns of an electrically-conductive material such as a metal wire, and the external transmitter inductive coil can be provided in, on, or with a belt designed to be placed externally around the part of the patient's body within which the receiver inductive coil is implanted. For appropriate power transfer from the external transmitter inductive coil to the implanted receiver inductive coil, at least a portion of the implanted receiver inductive coil typically will and should be disposed within an imaginary plane that passes through the part of the patient's body within which the receiver inductive coil is implanted and that is defined by the external transmitter inductive coil. It could be that the entirety of the implanted receiver inductive coil is disposed with this imaginary plane. Like the external transmitter inductive coil, the implantable receiver inductive coil can be one, two, or more turns of an electrically-conductive material such as a metal wire. The implantable device can be a blood pump, a ventricular assist device (VAD), or some other type of implantable medical device that requires power to operate, and the part of the patient's body within which the device/receiver-coil is implanted can be an arm, a leg, a torso, or a head of the patient.

These and other aspects, features, objects, and advantages of the invention will become apparent through reference to the following description, drawings, and claims. It is noted that aspects of the embodiments described herein are not mutually exclusive and can exist in various combinations and permutations even if not specifically indicated herein.

BRIEF DESCRIPTION OF THE DRAWINGS

In the drawing(s), like reference characters generally refer to the same or similar parts throughout the different views. The drawings are intended to illustrate the details of one or more embodiments according to the invention and/or the principles of the invention.

DESCRIPTION

Figure 1:
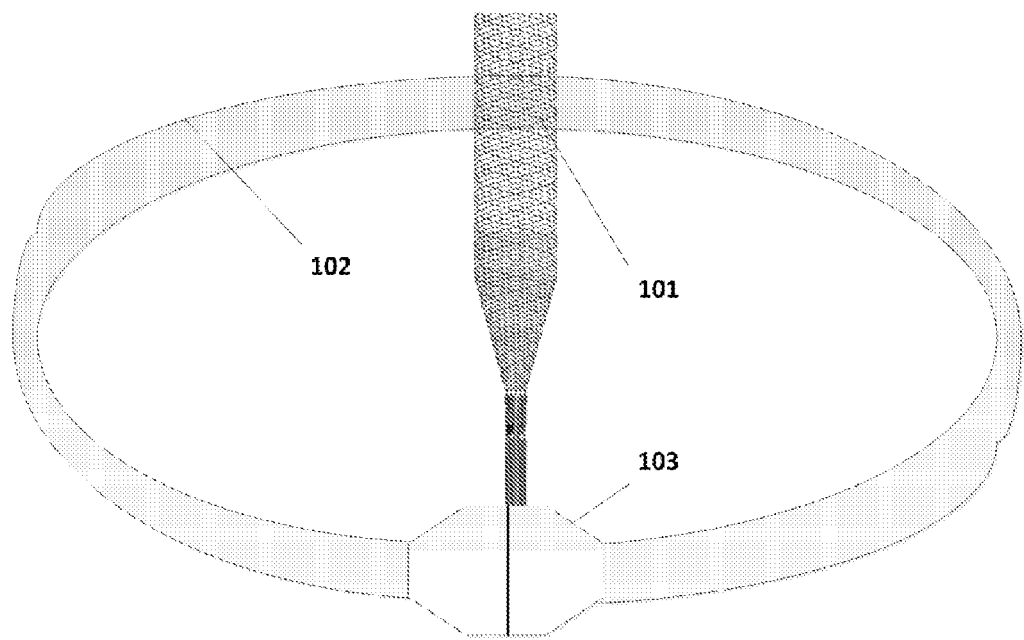
FIG. 1 depicts an external belt 102 surrounding an implantable receiver coil 101; the belt can be opened and closed using a buckle 103.

The invention relates to an external transmitter inductive coil that can be provided in, on, or with a belt designed to be placed externally around a part of a body of a patient. Referring to FIG. 1, a surrounding belt 102 is depicted with a medical stent 101 therewithin. The stent 101 has built into it or incorporated within it a receiver coil of one or more turns of electrically-conductive material such as copper wire, for example. The belt 102 has in or on it, around its entire length, one or more turns of a transmitter coil. Like the receiver coil, the transmitter coil can have one or more turns of electrically-conductive material such as copper wire, for example. Together, the external belt 102 with the transmitter coil and the implantable medical device (such as a stent) with the receiver coil, can be considered a wireless power transfer system. In use, the transmitter coil is located externally around the chest of a patient or around some other part of the patient's body such as an arm, a leg, a head, or another part of the patient's torso, and the receiver is implanted within that part of the patient's body, such that electromagnetic power inductively transmitted from the surrounding coil of the belt 102 reaches and is wirelessly received by the patient-implanted receiver coil from all angles and directions.

This physical arrangement of the external surrounding transmitter coil and the internally implanted receiver coil (that is disposed at least partially within an imaginary plane cutting through the patient's body and that is formed or defined by the surrounding external transmitter coil) can be referred to as a coplanar arrangement. And the system of the external transmitter coil and the implanted receiver coil thus can be referred to as a coplanar energy transfer (CET) system.

CET is different than a known and common technique referred to as transcutaneous energy transfer (TET). TET only transfers energy through an area of the skin of a patient to a shallowly-implanted receiver just under that area of the skin. CET, in sharp contrast, involves surrounding the implanted receiver coil by placing or wrapping a transmitter coil completely around the part of the patient's body within which the receiver coil is implanted. If the receiver coil is disposed within the brain of the patient, for example, then CET involves disposing the transmitter coil externally around the corresponding part of the head of the patient such that an imaginary plane defined by the surrounding transmitter coil extends through at least a portion of the brain-implanted receiver coil. If the receiver coil is instead implanted within the descending aorta of the patient's vasculature, CET involves disposing the transmitter coil externally around the corresponding part of the patient's chest such that the imaginary plane defined by the surrounding transmitter coil extends through at least a portion of the aorta-implanted receiver coil. These are just two examples of where the transmitter and receiver coils could be located, and other locations are possible such as the arm or the leg of a patient.

The stent 101 of FIG. 1 has built into it or incorporated within it the receiver coil, as indicated previously, and in this regard it is noted that the receiver inductive coil can comprise one or more electrically conductive fibers or strands that are among the various fibers or strands that together constitute the stent 101. These fibers or strands that comprise the receiver inductive coil can be electrical wires and can be coated with an electrical insulator. The receiver inductive coil can be built into or incorporated within the stent 101 in a variety of other ways.

In one embodiment, the receiver coil is not built into the device with which it is associated. In this embodiment, the implantable receiver coil is operatively connected (such as by an electrical wire connection) to the implantable device to be able to provide wirelessly-received power to the implanted device but otherwise could be physically separate from and not an integral part of the device itself.

In another embodiment, the receiver coil is built into the device with which it is associated.

In one embodiment, the receiver coil is a stent 101 as shown in FIG. 1 as the device with which the implantable receiver coil is associated, In addition to VADs, the receiver coil can be associated with a variety of other types of implantable devices, including, for example, a constant glucose meter (CGM), a bloodpressure sensing device, a pulse sensing device, a pacemaker, implantable cardioverter defibrillators (IDC), digital cameras, capsule endoscopies, implanted slow release drug delivery systems (such as implanted insulin pump) a nerve stimulator, or an implanted ultrasound device.

In operation, the CET system generates lower radio-frequency (RF) energy densities than TET systems. Because CET uses a surrounding external belt-like transmitter coil, the RF energy that is inductively transmitted into the patient's body from the transmitter coil is spread out and not concentrated or focused into or onto a particular spot or area of the patient's body. Using CET, the transmitted energy is spread out over the external transmitter coil of the CET, resulting in transmitted field strength and power density levels that are lower than TET systems. Also using a surrounding external belt-like transmitter coil eliminate misalignment problem and reduce dramatically the misplacement problems.

It is noted that a power source must be associated with the external transmitter coil to provide that coil with the power that it will then wirelessly transmit for receipt by the implanted receiver coil. A controller unit also typically will be provided to regulate the operation of the transmitter coil Like the transmitter coil, both the power source and the controller will be external to the patient. The external source can be an AC current source, and the transmitter coil can be electrically connected to the AC current source. It also is noted that the transmitter coil can be a transceiver—that is, capable of both transmitting and receiving.

Providing an Optimal Load to the Receiver Resonance Structure:

In one embodiment according to the invention, the device with which the implantable receiver coil is associated is a ventricular assist device (VAD). In this embodiment a DC-to-DC converter is employed to provide an optimal load to the receiver inductive coil. The DC-to-DC converter is designed to automatically adjust to provide a constant or substantially constant selected optimum load to the receiver inductive coil. Typically, the DC-to-DC converter is implanted within the patient's body along with the receiver inductive coil and the VAD.

Figure 2:
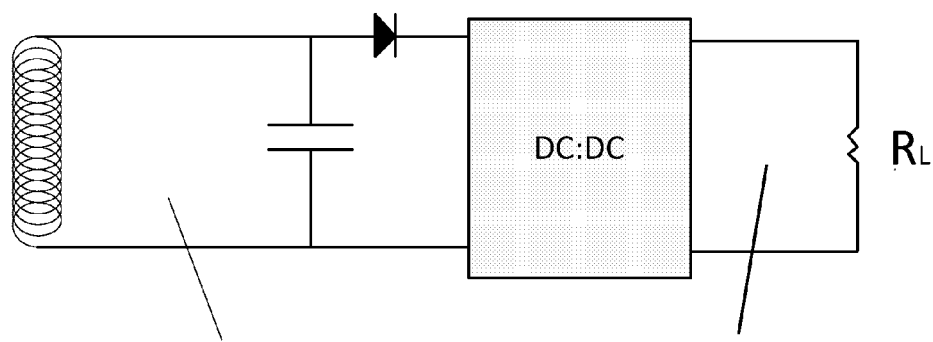
FIG. 2 shows an implantable circuit with a DC-to-DC converter coupled to the implantable receiver resonance structure 202. The load $R_1$ can be a VAD or any other power consuming implantable device.

FIG. 2 shows a DC-to-DC converter disposed between the receiver inductive coil and the resonance structure 202 (on the left) and a load $R_L$ (on the right). Load 201 may be a VAD or a constant glucose meter, or another implantable device described herein. As shown in FIG. 2, the circuit can also include a half or full-wave rectification (i.e., using a diode or diode bridge). As shown in FIG. 2, resonance structure 202 is formed by the receiver inductive coil and a capacitor. However the external transmitter inductive coil may also be associated with a capacitor to form a transmitter or transceiver resonance structure.

Figure 3:
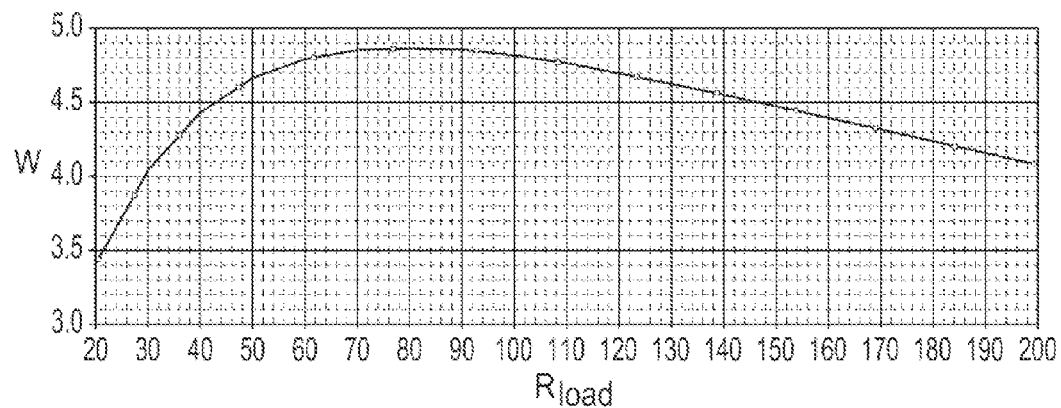
FIG. 3 is a graph showing a relationship between output power and load resistance.

The optimum load can be determined with reference to FIG. 3 which shows a relationship between power harvesting (W) and an $R_{load}$ value for a particular circuit, where $R_{load}$ is the internal resistance of whatever load is associated with the receiver inductive coil. While merely exemplary, the graph of FIG. 3 shows that the best power harvesting for the circuit is 80 Ohms or about 80 Ohms. A load with a resistance lower than 80 Ohms will reduce the voltage on the load and thereby reduce the harvested power, and a load with a resistance higher than 80 Ohms will reduce the current and thereby reduce the harvested power. The shape of the curve in the graph of FIG. 3 is determined by the function (26), provided below. In the case of a VAD, the resistive load represented by the VAD's motor will change as the mechanical load on the motor changes, and the depicted circuit (in FIG. 2) with the DC-to-DC converter is what is used to automatically adjust and provide a substantially constant and optimum load to the receiver inductive coil.

Figure 4:
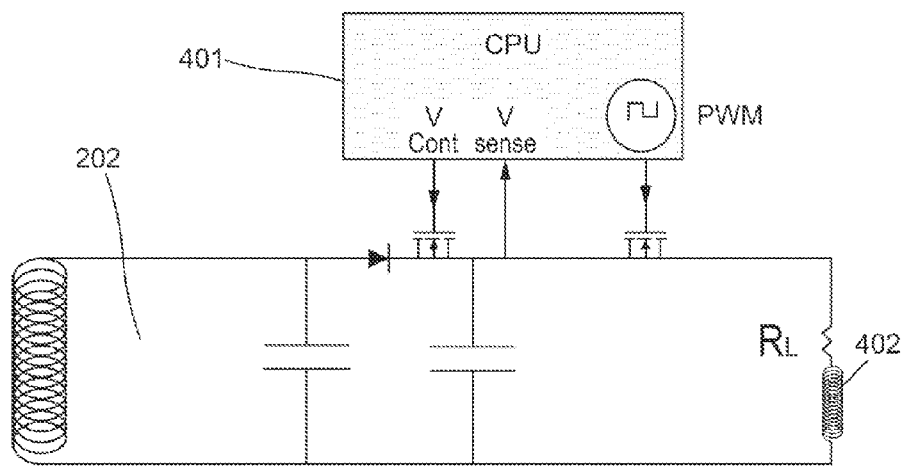
FIG. 4 shows an alternative circuit coupled to the implantable receiver coil. The circuit has the same resonance structure 202 but uses the inductiveness of the implant VAD 402 and controller 401 as a DC to DC.

In case of medical implant with high inductive load, like a VAD or implanted slow release drug delivery system that uses a motor, an alternative to the circuit of FIG. 2 is the circuit shown in FIG. 4. The circuit of FIG. 4 can be employed to adjust to an ideal working point of the receiver inductive coil (or, more accurately, of the receiver resonance structure which, as described above, is the combination of the receiver coil and its associated capacitor) when the device with which the implantable receiver coil is associated is a VAD.

An implant with a brushless DC motor, like a VAD, needs adjustable power control to receive exactly the needed mechanical power. As shown in FIG. 3 and by function (26) below and as described above, the best power harvesting is achieved with the optimum $R_{load}$. In this situation, a high quality motor controller, such as MOTION EN Speed Controller Series SC 1801 F (Faulhaber GmbH & Co. KG, Schönaich, Germany), can be used as a DC-to-DC converter for adjusting the $R_{load}$ to the optimum value using PWM (pulse width modulation). As shown in FIG. 4, a voltage and motor PWM controller 401 gives full control over the working point without any additional measures.

By controlling the voltage and the DC-to-DC rate, the optimum $R_{load}$ can be achieved. The brushless DC motor of the VAD can be simulated with an equivalent resistor and inductor circuit. The speed of the motor is controlled using PWM as the motor input voltage, and the duty cycle is adjusted according to the needed speed. The coils of the VAD's motor flat the current just as is done in DC-to-DC voltage conversion. In this way, the VAD's motor is used as a DC-to-DC converter, and the reflected motor load is dependent on the conversion rate.

Adding a voltage sensor with voltage control adds the capability to select the voltage in the receiver circuit. This gives full control on the reflected load (using the PWM mechanism) and on the used power by controlling the voltage (using the voltage control). For example, a LPC1102 chip can be used for (NXP Semiconductors N.V., Eindhoven, Netherlands) voltage sensing while an internal PWM engine and can control the voltage by using a transistor like SI8409DB (NXP Semiconductors) for closing the inline from the resonance structure 202.

The voltage control can be done in several ways. One example is harvesting control on/off measured, as shown in FIG. 4, in the implanted receiver electronics itself. Another example is transmitting power control in the external transmitter/transceiver primary electronics that closes the loop according to the $V_{sense}$ in the receiver.

Locking the Receiver and the Transmitter:

Once placed within the body of a patient, the receiver coil shape can be distorted or modified from its at-rest shape and also can move over time to some extent as the patient moves, all depending on the particular location internally within the patient's body where the receiver coil is placed. With changing of its shape, the resonance frequency of the receiver coil changes. It is important for the transceiver resonance structure to be able to automatically find the receiver's resonance and adjust the transceiver's resonance to that found for the receiver and lock to that found resonance. In other words, the transceiver must have the capability to detect the receiver's resonance frequency and then lock to that detected receiver's resonance frequency.

Figure 14:
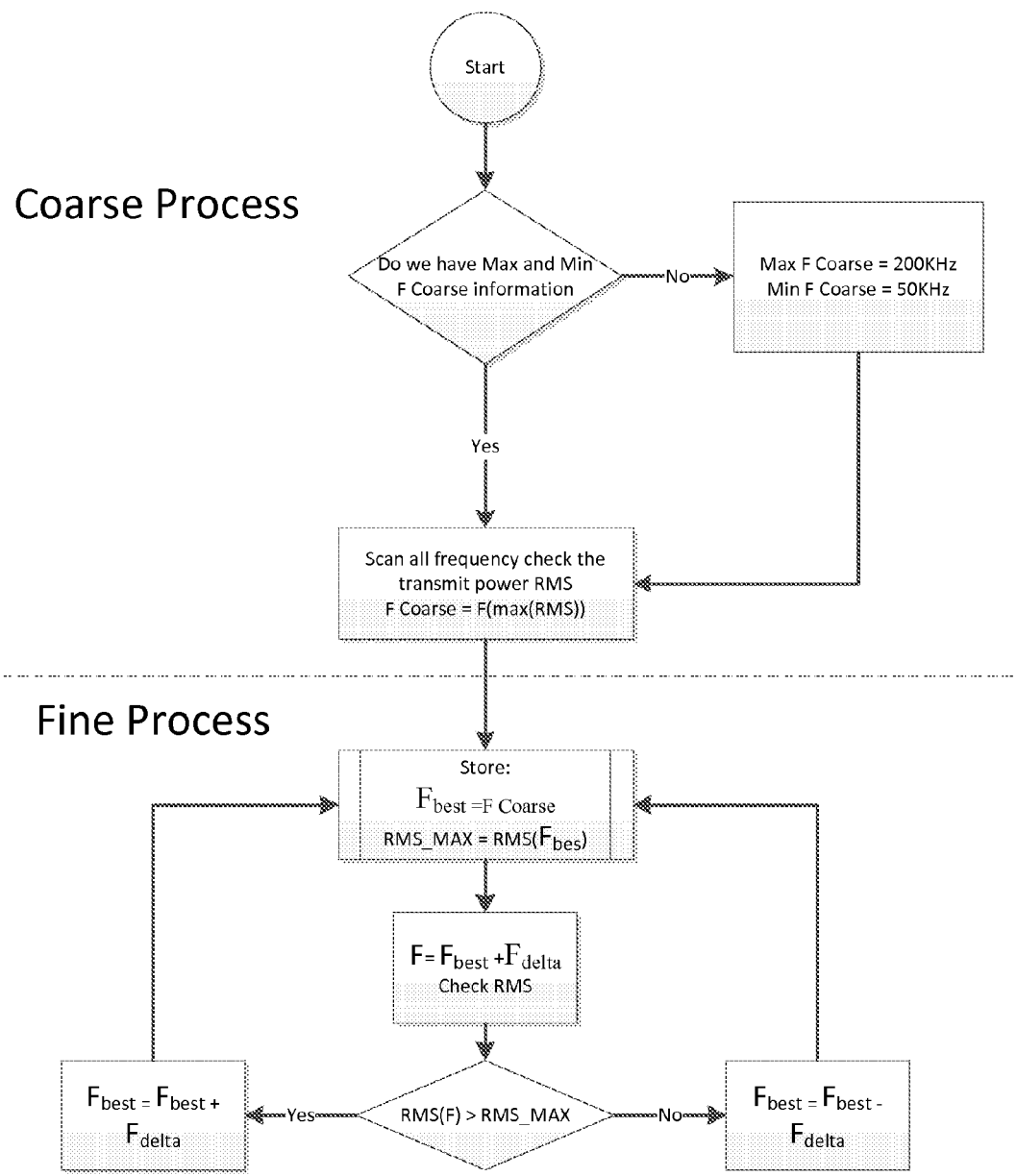
FIG. 14 is a flow chart of coarse and fine resonance frequency detection.
Figure 15:
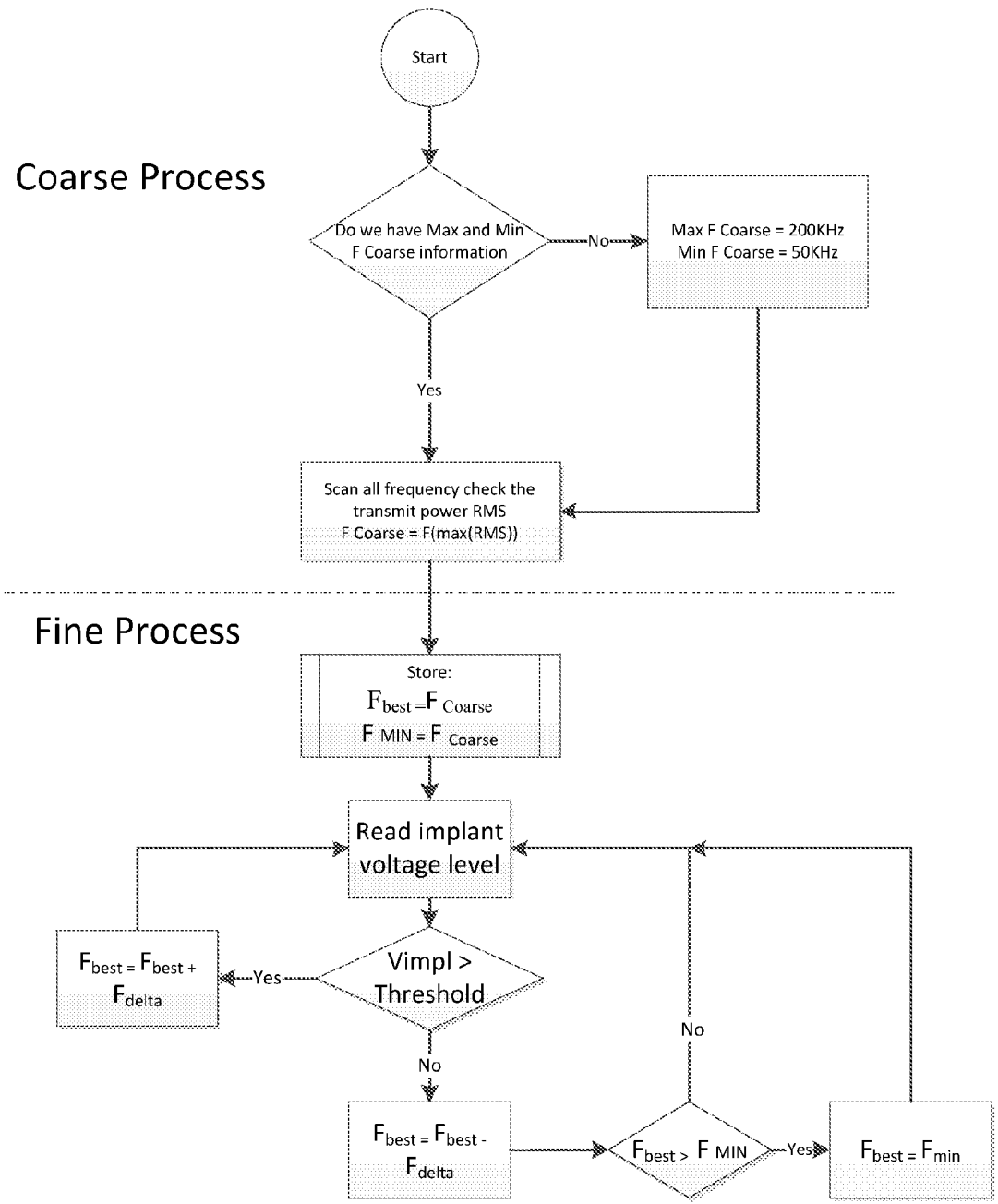
FIG. 15 is a flow chart of coarse and fine frequency base power control.

As described in FIG. 14 and in FIG. 15 the transceiver can detect the receiver's resonance frequency in two phases.

First, in a coarse phase, when no pre-detected frequency is available, the transceiver uses a fast frequency detection process to roughly detect the receiver resonance frequency or else just start at some predetermined frequency. Second, in a fine phase that occurs after the coarse phase, the transceiver uses an ongoing process of fine tuning to detect the receiver resonance frequency.

The main difference between the two procedures is the simplicity of the solution. FIG. 15 describes a very simple system where the coarse phase detects roughly the resonance, which then becomes the minimum frequency limit. (The system of FIG. 15 doesn't use the resonance frequency exactly, it uses a frequency above (or below) the resonance and then controls the transfer power by tuning the frequency). This is a simple system and it can work in strong coupling environment like the CET system. In other instances, when the coupling is lower due to distance or receiver/transceiver size/quality it is necessary to use the exact resonance frequency to be able to transfer the needed power.

FIG. 14 describes the fine process that occurs after the first coarse adjust approximately determines the transmitter resonance. In the coarse phase, a microcontroller (MCU) associated with the transceiver resonance structure can have preliminary information about the receiver resonance frequency. The MCU will change the transceiver's driver frequency one after the other and detect the root mean square (RMS) current in the one or more coils of the transceiver. At the end of this phase, the MCU has the result of the entire frequency spectrum, and it can automatically select (as a result of its software programming) the best first coarse frequency, $F_{coarse}$.

After the coarse phase, the fine phase begins, in which the MCU's software programming dictates the selected frequency from the coarse phase as the best known resonance, $F_{best}$. Once in the fine phase, the MCU stores the RMS current, adds single $F_{delta}$ to the previous frequency and stores that RMS current. By comparing these two RMS currents, the transceiver's MCU determines whether to add $F_{delta}$ or to reduce $F_{delta}$ from the previous $F_{best}$. The equation used is as follows: $F_{best}=F_{best}+/-F_{delta}$. Then, the tranceiver's resonance frequency is locked to the receiver's resonance frequency until the next fine phase process occurs. The fine phase process can occur periodically every $T_{fine}$.

Figure 5:
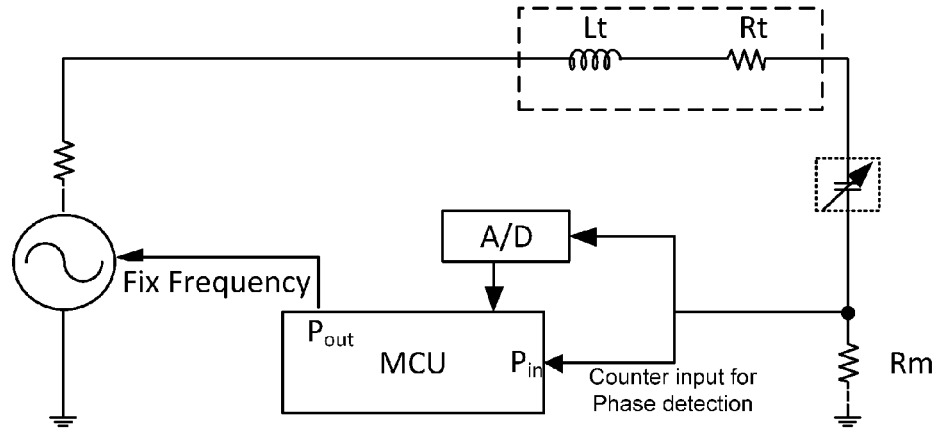
FIG. 5 is a circuit that can be used to lock the external transceiver resonance frequency to the implanted receiver resonance frequency.
Figure 6:
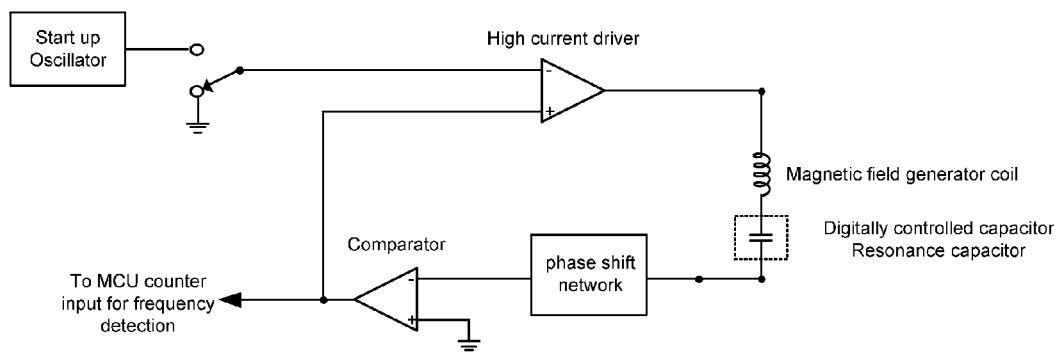
FIG. 6 is another circuit that can be used to lock the external transceiver resonance frequency to the implanted receiver resonance frequency.

Locking the transceiver resonance to the detected receiver resonance involves the transceiver coil automatically adjusting its capacitors, which can be accomplished using either the circuit shown in FIG. 5, or the circuit shown in FIG. 6, each of which is a resonance LC (inductance and capacitance) structure.

Figure 16:
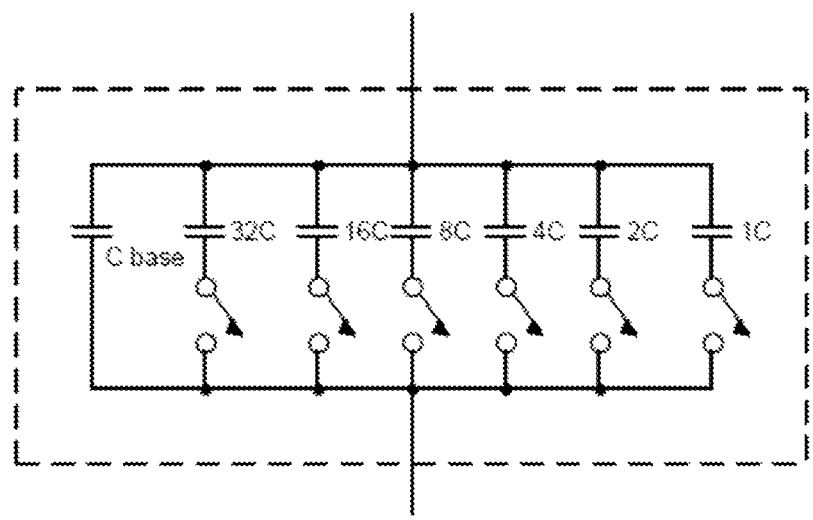
FIG. 16 shows a configurable capacitor for use with a circuit for locking the external transceiver resonance.

In the circuit of FIG. 5, the MCU forces a fix frequency by generating $P_{out}$ pulse in the requested frequency and push the driver circuit. In so doing, the MCU thereby calibrates the configurable capacitor to get resonance. The MCU receives the feedback phase, and adjusts it to the resonance. In resonance, the feedback phase $P_{in}$ should be exact as the generated one $P_{out}$. The MCU then compares the output $P_{out}$ to the input $P_{in}$ to validate the resonance. The MCU should adjust the capacitors according to the phase until $P_{in}=P_{out}$ In the circuit of FIG. 6, the circuit is a self-oscillating circuit, and thus is always in resonance, however the MCU can adjust the frequency by changing the capacitors. The MCU can add capacitors to the capacitors array or remove capacitors as described in FIG. 16.

Although FIGS. 5 and 6 show two particular circuits that can be used, it is noted that a variety of variants of phase locked loop (PLL) algorithms and implementing circuits can be used to compensate for impedance changes of the coils by adjusting capacitor value.

Figure 7:
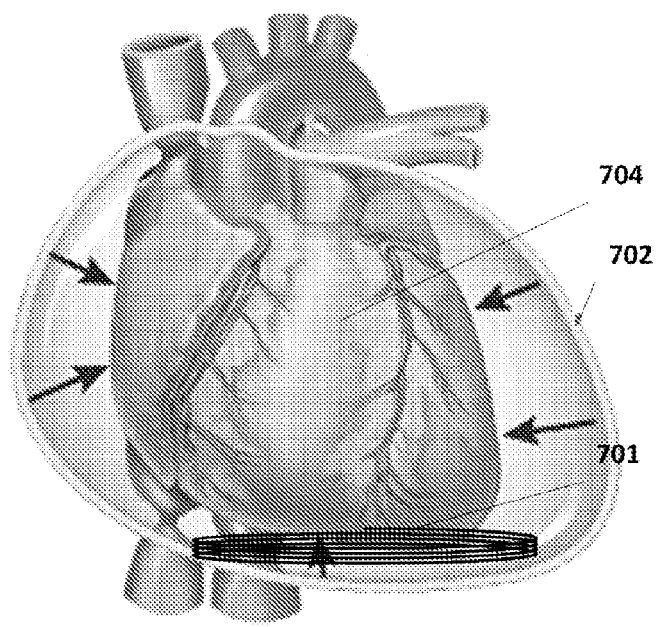
FIG. 7 shows ring coil 701 implanted in the bottom of the pericardium sack 702.
Figure 8:
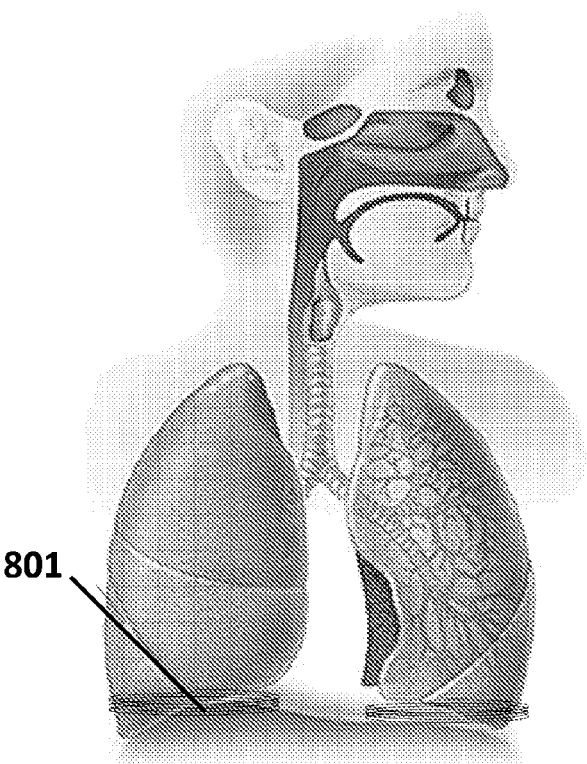
FIG. 8 shows two ring coil 801 implanted in the bottom of the pulmonary cage.
Figure 9:
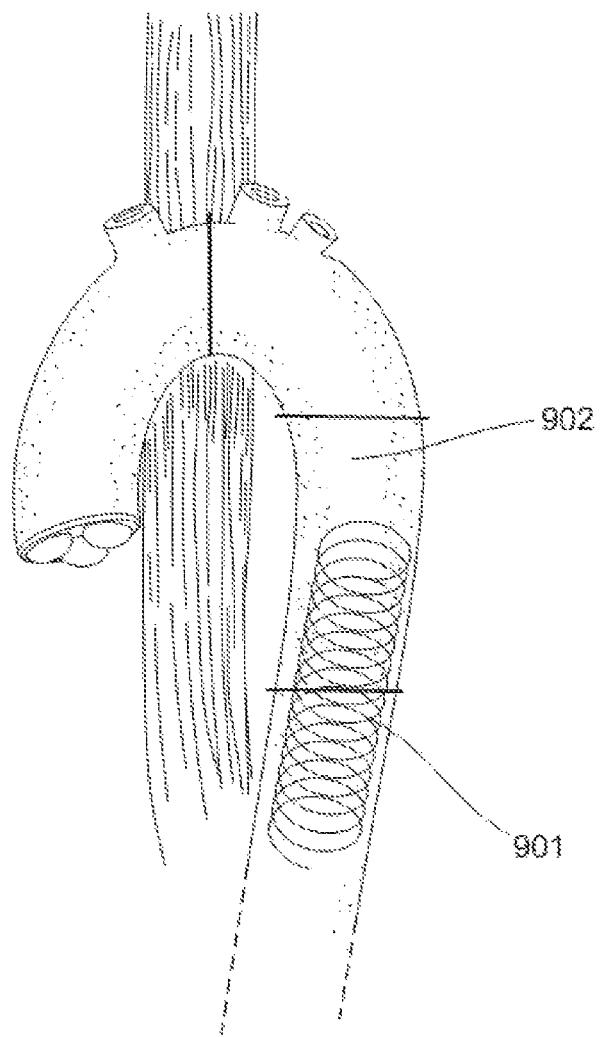
FIG. 9 shows stent base ring coil 901 located in the descending aorta 902.

Placement in a Patient's Body of the Receiver Resonance Structure:

The receiver inductive coil can be placed within the body of a patient at a variety of internal locations. FIGS. 7, 8, and 9 illustrate three particular examples of a placement location inside the body of a patient.

As shown in FIG. 7, the receiver coil 701 may be placed in the base of the flat part of the pericardia 702, which surrounds the heart 704. The main added value in placing the receiver coil 701 in the pericardia 702 with a VAD is that the pericardia 702 is relatively flat and open in typical VAD surgery. The receiver coil 701 can be glued to the pericardia 702 boundaries, e.g., with surgical glue.

In FIG. 8, it is shown that the receiver coil 801 of a VAD can be placed in the pulmonary cage. One advantage of placing the coil 801 in the pulmonary cage is that the VAD will not disturb the magnetic power harvesting, and that pulmonary cage is relatively easy to access during the VAD surgery.

As shown in FIG. 9, the receiver coil 901 may also be placed in an artery 902. The Aorta or the Vena Cava are particularly well-suited for placement of the receiver coil 901 because each is oriented vertically with respect to a plane that cuts in a cross section through the torso of the patient. Placement of the receiver coil 901 in the Aorta or the Vena Cava also allows the receiver coil 901 to be associated with an implantable stent.

Further Disclosure Related to Providing an Optimum Load to the Receiver Resonance Structure:

Having presented various details of various embodiments according to the invention, some theory, equations, and calculations relevant to providing an optimum load to the receiver resonance structure will now be presented.

The ratio between the distance D from the transmitting coil to receiving coil and the wavelength λ is as follows:

$$\frac{D}{\lambda} = \frac{Df}{c}, \tag{1}$$

where f is the transmitting frequency and $c=3\cdot10^8$ m/s is the speed of light.

Given that the maximum distance $D_{max}$ does not exceed 0.4 m and the working frequency is f=100 kHz, the ratio $D_{max}/\lambda=0.00013\ll1$. Thus, we can conclude that the receiving coil is in the quasi-static area, and we can neglect the effects of the phase difference due to the wave propagation.

The amplitude of the voltage induced in the receiving coil according to the Faraday's law [1] is as follows:

$$v_r(t) = -\frac{d\Phi}{dt} = -\frac{d}{dt}(B \cdot a), \tag{2}$$

where Φ is the magnetic flux through the receiving coil, B is the magnetic flux density, and a is the effective area of the receiving coil.

To estimate the maximum induced voltage (2), assume that the receiving coil is located coaxially with the transmitting coil at its center, where the magnetic flux density B can be calculated as follows [1]:

$$B = \frac{\mu_r \mu_0 I_t N_t}{2R_t} \sin(2\pi f t), \quad (3)$$

where $\mu_r$ is the relative permeability of media, $\mu_0 = 4\pi 10^7$ V·s/(A·m) is the permeability of vacuum, $I_t$ is the amplitude of the current in the transmitting coil, and $R_t$ and $N_t$ are the radius and number of turns of the transmitting coil correspondingly.

The effective area of the receiving coil can be calculated as follows:

$$a = \pi R_r^2 N_r, \quad (4)$$

where $R_r$ and $N_r$ are the radius and the number of turns of the receiving coil correspondingly.

Substituting (3) and (4) into (2) and differentiating with respect to the time, gives the following expression for the amplitude of the voltage induced in the receiving coil:

$$V_r = 2\pi f \frac{\mu_r \mu_0 I_t N_t}{2R_t} \pi R_r^2 N_r. \quad (5)$$

The transmitting and the receiving coils can be seen as two coupled inductors, as follows:

$$\begin{cases} v_t = L_t \frac{di_t}{dt} - M \frac{di_r}{dt} \\ v_r = -M \frac{di_t}{dt} + L_r \frac{di_r}{dt} \end{cases}, \quad (6)$$

where $v_t$ and $v_r$ are the transmitter and receiver coils voltages, $i_t$ and $i_r$ their currents, and $M$ is the mutual inductance.

Assuming that the current in both coils is a sine-wave of frequency $\omega = 2\pi f$, (6) can be written as follows:

$$\begin{cases} v_t = j\omega L_t i_t - j\omega M i_r \\ v_r = -j\omega M i_t + j\omega L_r i_r \end{cases}. \quad (7)$$

The mutual inductance $M$ can be found from the open circuit experiment, where $i_r = 0$:

$$\begin{cases} v_t|_{i_r=0} = j\omega L_t i_t \\ v_r|_{i_r=0} = -j\omega M i_t \end{cases}. \quad (8)$$

Rearranging the second equation of (8) with respect to $M$ and substituting (2)-(5) gives us:

$$M|_{i_r=0} = -\frac{v_r}{j\omega i_t} = -\frac{-\frac{d}{dt}(B \cdot a)}{j\omega i_t} = \frac{\mu_r \mu_0 N_t}{2R_t} \pi R_r^2 N_r = 3.9 \ \mu H. \quad (9)$$

The value of $M$ obtained in (9) increases as a function of the relative permeability $\mu_r$ of the receiver core.

Figure 10:
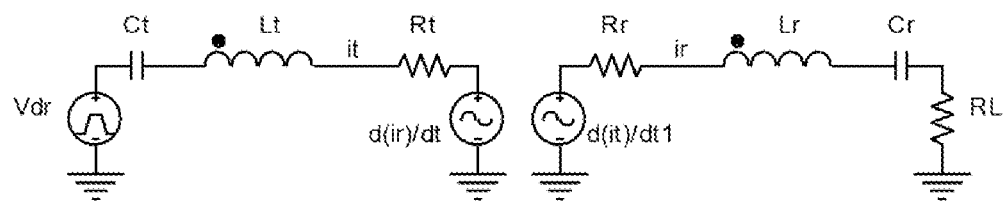
FIG. 10 shows a model circuit for calculating the efficiency of energy transmission.

For the purpose of efficiency calculation, assume that the transmitter coil is loaded with a series resonant capacitor and the receiver coil is loaded to form a series resonant circuit as describe in FIG. 10.

The transmitter current is calculated using the coupled-inductor model (7), as follows:

$$i_t = \frac{v_s}{R_t + \frac{(\omega M)^2}{R_r + R_L}}, \quad (24)$$

where $v_s = 2V_{DD}/\pi$ is the effective voltage of the source $V_{dr}$ at the first harmonic of the excitation frequency, $R_t$ is the active resistance of the transmitter coil, $R_r$ the active resistance of the receiver coil, and $R_L$ is the load resistance.

The amplitude of the load voltage is given by:

$$V_L = \frac{2\omega M V_{DD}/\pi}{R_t + \frac{(\omega M)^2}{R_r + R_L}} \cdot \frac{R_L}{R_r + R_L} = \frac{2\omega M V_{DD}/\pi}{R_t(R_r + R_L) + (\omega M)^2} \cdot R_L, \quad (25)$$

where $V_{DD}$ is the supply voltage of the half-bridge driver of the transmitter.

From here, the load power is given by:

$$P_L = \frac{V_L^2}{2R_L} = \frac{2(\omega M V_{DD}/\pi)^2 R_L}{(R_t(R_r + R_L) + (\omega M)^2)^2}. \quad (26)$$

Differentiating (26) with respect to $R_L$ gives the load resistance that maximizes the load power, as follows:

$$R_{Lopt} = R_r + \frac{(\omega M)^2}{R_t}. \quad (27)$$

Substituting (27) into (26) yields:

$$P_{Lopt} = 0.5 \frac{(V_{DD}/\pi)^2 (\omega M)^2 / R_t}{R_t R_r + (\omega M)^2}. \quad (28)$$

Rearranging (28) with respect to the driver voltage gives:

$$V_{DD} = \frac{\pi}{\omega M} \sqrt{2 P_{Lopt} R_t (R_t R_r + (\omega M)^2)}. \quad (29)$$

The input power is:

$$P_t = \frac{V_{DD}}{2\pi} \int_0^{\pi/\omega} i_t(t) \, dt = 2 \left( \frac{V_{DD}}{\pi} \right)^2 \frac{R_r + R_L}{R_t(R_r + R_L) + (\omega M)^2}, \quad (30)$$

while its optimal value considering (27) is:

$$P_{topt} = \left( \frac{V_{DD}}{\pi} \right)^2 \frac{2R_r + (\omega M)^2 / R_t}{R_t R_r + (\omega M)^2}. \quad (31)$$

Dividing (29) by (31) gives the efficiency of the wireless power transmission corresponding to the optimum load resistance:

$$\eta_{opt} = \frac{P_{Lopt}}{P_{topt}} = 0.5 \frac{1}{1 + \frac{2R_r R_t}{(\omega M)^2}}. \quad (32)$$

The general expression for the efficiency is:

$$\eta = \frac{P_L}{P_t} = \frac{(\omega M)^2}{R_t(R_r + R_L) + (\omega M)^2} \cdot \frac{R_L}{R_r + R_L}. \quad (33)$$

Differentiating (33) with respect to $R_L$ gives the load resistance that maximizes the efficiency:

$$R_{L\eta max} = \sqrt{R_r^2 + \frac{(\omega M)^2 R_r}{R_t}}. \quad (34)$$

The maximum efficiency can be calculated by substituting (34) into (33).

$$\eta_{max} = 0.5 \frac{1}{1 + \frac{2R_r R_t}{(\omega M)^2}}. \quad (32)$$

The maximum efficiency and maximum load power for the parallel-loaded receiver is identical to that of the series one. The optimal load resistance and maximizing the efficiency for the parallel-loaded receiver differ from (27) and (34). However, the derivation is similar. The specific formulae for the load resistance is not developed here and instead we find the optimal resistance using computer simulations tool like PSPICE® (Cadence Design Systems, San Jose, Calif.), a full-featured, native analog and mixed-signal circuit simulation tool.

Figure 11:
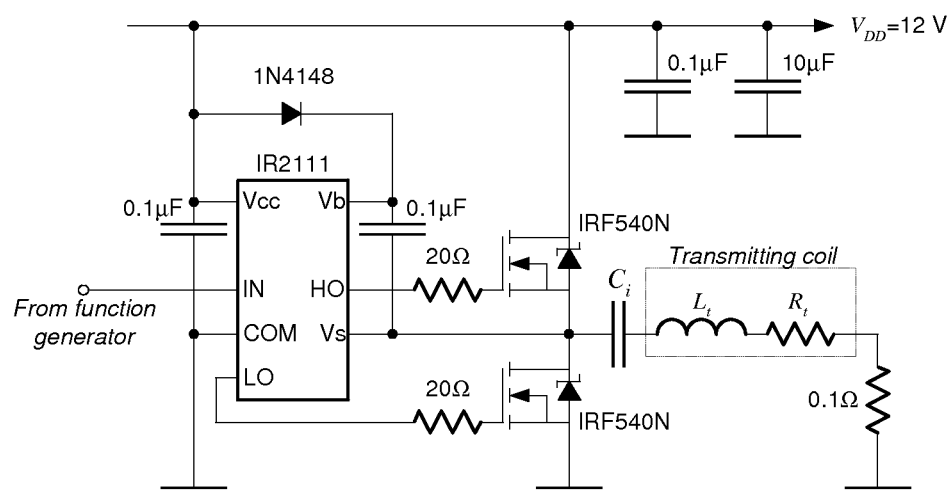
FIG. 11 shows a schematic of a series-loaded receiver circuit.

The circuit shown in FIG. 11 is a series-loaded receiver. The source Vdr is built from two BUZ11 N-MOSFETs driven by the IR2111 gate driver. The 0.1 Ohm resistor is used for the transmitter current monitoring. Both the transmitter and receiver capacitors are chosen with low ESR. The load resistance is chosen as $R_L$=0.5 Ohm, and the driver voltage $V_{DD}$=12 V. Substituting these values and the other setup parameters ($R_t$=1 Ohm, $R_r$=0.65 Ohm, M=2.056 µH) into (26) gives for $P_L$=3.16 W. The measured voltage amplitude on the load resistance is 1.75 V, which corresponds to $P_L$=3.1 W. The input power drawn from the power supply is $P_{in}$=$V_{DD}$/π·I=12/3.14·2.8=10.7 W. The efficiency is η=$P_L$/$P_{in}$=28%. It is noted that the load resistance is not optimized for the maximum output power.

Figure 12:
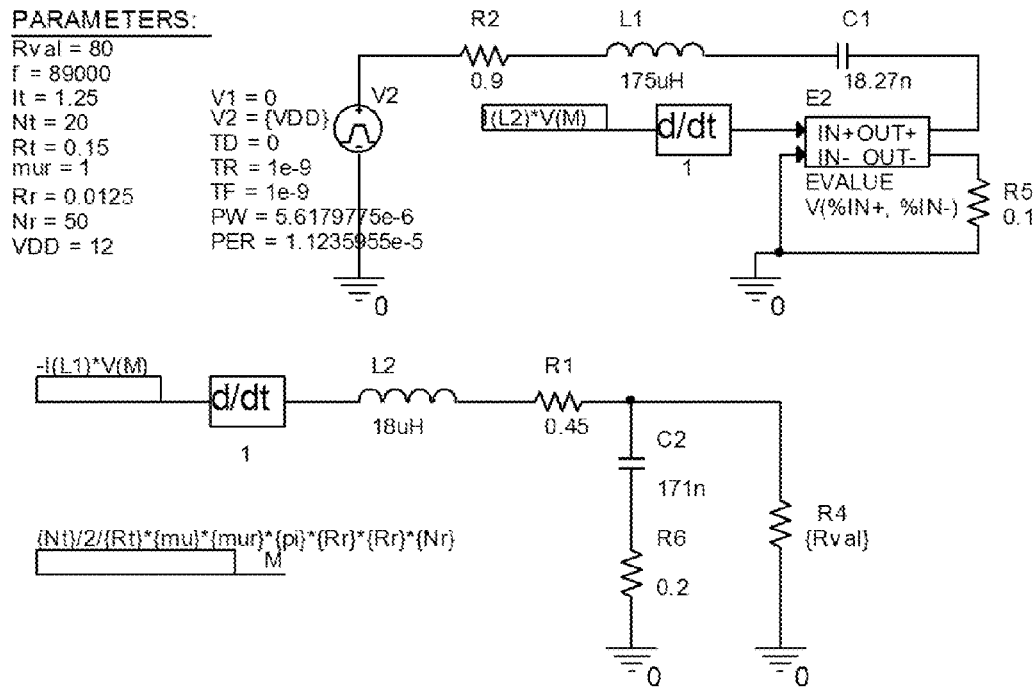
FIG. 12 shows a schematic of a parallel-loaded receiver circuit.

The circuit shown in FIG. 12 is a parallel-loaded receiver. The source V2 is built from two BUZ11 N-MOSFETs driven by the IR2111 gate driver. The 0.1 Ohm resistor is used for the current monitoring. Both the transmitter and receiver capacitors are chosen with low ESR. Substituting the model parameters into (29) gives $V_{DD}$=11.5 V for $P_L$=5 W. Computer simulations have shown that the maximum load power of 4.85 W is obtained for $R_L$=80 Ohm. This result closely correlates with laboratory measurements, where an output power of 4.5 W was measured for $V_{DD}$=12 V. The input power drawn from the power supply is $P_{in}$=$V_{DD}$/π·I=12/3.14·4.2=16.05 W. The efficiency is $\eta_7$=$P_L$/$P_{in}$=28%.

Figure 13:
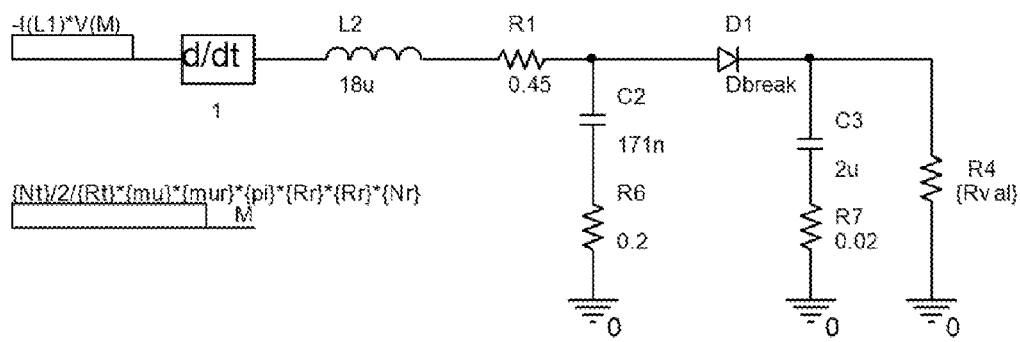
FIG. 13 shows a schematic whereby a simple single-phase rectifying circuit is added to a receiver.

Inserting a simple single-phase rectifying circuit before R4, as shown in the circuit in FIG. 13, takes about 0.2 W dissipated on the diode with 2 A peak diode current and 44 V peak diode reverse voltage. The peak voltage on the receiver capacitor is 25 V, and the peak voltage on the transmitter capacitor is 500 V.

Various modifications may be made to the embodiments disclosed herein. The disclosed embodiments and details should not be construed as limiting but instead as illustrative of some embodiments and of the principles of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A system for wirelessly powering a ventricular assist device (VAD) implanted within a body of a patient, comprising:
    a receiver inductive coil associated with the VAD and configured to be disposed in the pleural cavity of the patient's body to wirelessly receive inductively-transferred electromagnetic power and provide that received power to the VAD; and
    a transmitter inductive coil comprising one or more turns of electrically-conductive material that are configured to surround the pleural cavity by being disposed externally and completely around a part of the patient's body within which the pleural cavity is located, the transmitter inductive coil configured to inductively transfer electromagnetic power to the receiver inductive coil.

2. The system of claim 1 wherein at least one capacitor is associated with the transmitter inductive coil to form a transceiver resonance structure.

3. The system of claim 1 wherein at least one capacitor is associated with the receiver inductive coil to form a receiver resonance structure.

4. The system of claim 1 wherein the transmitter inductive coil comprises a transceiver capable of both transmitting and receiving.

5. The system of claim 1 wherein the receiver inductive coil uses a coil of the VAD to adjust to an ideal working point of the receiver inductive coil.

6. The system of claim 1 further comprising a second receiver inductive coil and wherein the two receiver inductive coils are coupled in series and function together as a single receiver inductive coil.

7. The system of claim 1 further comprising a circuit associated with the receiver inductive coil and wherein the circuit detects the resonance frequency of the receiver inductive coil and locks the resonance frequency of the transmitter inductive coil to the resonance frequency of the receiver inductive coil.

8. The system of claim 1 further comprising a circuit associated with the transmitter inductive coil and wherein the circuit compensates and keeps the resonance frequency of the transmitter inductive coil locked to the resonance frequency of the receiver inductive coil when the shape and thus the impedance of the transmitter inductive coil changes.

9. The system of claim 1 wherein a DC-to-DC converter associated with the VAD automatically adjusts to provide a substantially constant and optimum load to the receiver inductive coils.

10. The system of claim 9 wherein the DC-to-DC converter is located between a motor of the VAD and the receiver inductive coil.

11. A system for wirelessly powering a ventricular assist device (VAD) implanted within a body of a patient, comprising:
- a receiver inductive coil associated with the VAD and configured to be disposed in a left pleural cavity of the patient's body to wirelessly receive inductively-transferred electromagnetic power and provide that received power to the VAD;
- a second receiver inductive coil associated with the VAD and configured to be disposed in a right pleural cavity of the patient's body to wirelessly receive the inductively-transferred electromagnetic power and provide that received power to the VAD; and
- a transmitter inductive coil comprising one or more turns of electrically-conductive material that are configured to surround the left and right pleural cavities by being disposed externally and completely around a part of the patient's body within which the left and right pleural cavities are located, the transmitter inductive coil configured to inductively transfer electromagnetic power to the receiver inductive coils.

12. The system of claim 11 wherein at least one capacitor is associated with the receiver inductive coils to form a receiver resonance structure.

13. The system of claim 12 wherein at least one capacitor is associated with each of the receiver inductive coils to form receiver resonance structures.

14. The system of claim 11 wherein the receiver inductive coils use a coil of the VAD to adjust to an ideal working point of the receiver inductive coils.

15. The system of claim 14 wherein each of the receiver inductive coils uses a coil of the VAD to adjust to an ideal working point of a respective receiver inductive coil.

16. The system of claim 11 further comprising a circuit associated with the receiver inductive coils and wherein the circuit detects the resonance frequency of the receiver inductive coils and locks the resonance frequency of the transmitter inductive coil to the resonance frequency of the receiver inductive coils.

17. The system of claim 11 wherein a DC-to-DC converter associated with the VAD automatically adjusts to provide a substantially constant and optimum load to the receiver inductive coils.

18. The system of claim 11 wherein at least one capacitor is associated with the transmitter inductive coil to form a transceiver resonance structure.

19. The system of claim 11 wherein the transmitter inductive coil comprises a transceiver capable of both transmitting and receiving.

20. The system of claim 11 further comprising a circuit associated with the transmitter inductive coil and wherein the circuit compensates and keeps the resonance frequency of the transmitter inductive coil locked to the resonance frequency of the receiver inductive coils when the shape and thus the impedance of the transmitter inductive coil changes.

* * * * *